United States Patent [19]

Matsumoto et al.

[11] Patent Number: 5,045,555
[45] Date of Patent: Sep. 3, 1991

[54] N-ALKYLBENZENESULFONYLCARBAM-OYL-5-CHLOROISOTHIAZOLE DERIVATIVES AND MICROBICIDES CONTAINING THE SAME

[75] Inventors: Kuniomi Matsumoto, Kanagawa; Mikio Munakata; Tadao Ishii, both of Tokyo; Tetsuro Watanabe, Kanagawa, all of Japan

[73] Assignee: Meiji Seika Kaisha Ltd., Tokyo, Japan

[21] Appl. No.: 569,508

[22] Filed: Aug. 20, 1990

Related U.S. Application Data

[63] Continuation of Ser. No. 227,660, Aug. 3, 1988, abandoned.

[30] Foreign Application Priority Data

Aug. 3, 1987 [JP] Japan ................... 62-192686

[51] Int. Cl.$^5$ .................. A01N 43/80; C07D 275/02
[52] U.S. Cl. .................. 514/372; 548/213
[58] Field of Search .......... 548/213; 514/372

[56] References Cited

U.S. PATENT DOCUMENTS 3,523,121  8/1970  Lewis et al. ............ 548/213
4,105,431  8/1978  Lewis et al. ............ 71/67

FOREIGN PATENT DOCUMENTS 0228247 12/1984 Japan .................. 514/372

OTHER PUBLICATIONS

S. Lewis, G. Miller, E. Szamborski and M. Hausman, "Isothiazoles III: 2-Carbamoyl-4-Isothiazolin-3-Ones", Journal of Heterocyclic Chemistry, vol. 8, No. 4, 1971, pp. 587-589.

Primary Examiner—Diana Rivers
Attorney, Agent, or Firm—Sughrue, Mion, Zinn, Macpeak & Seas

[57] ABSTRACT

A novel compound represented by the formula (I)

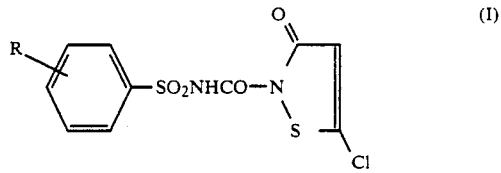

wherein R represents a lower alkyl group having 1 to 4 carbon atoms which has an intense microbicidal activity over a wide range of microorganisms and is applicable to a microbicide.

5 Claims, No Drawings

N-ALKYLBENZENESULFONYLCARBAMOYL-5-CHLOROISOTHIAZOLE DERIVATIVES AND MICROBICIDES CONTAINING THE SAME

This is a continuation of application Ser. No. 227,660 filed Aug. 3, 1988, now abandoned.

FIELD OF THE INVENTION

The present invention relates to novel N-alkylbenzenesulfonylcarbamoyl-5-chloroisothiazole derivatives, and microbicides containing the same.

The microbicide of the present invention is widely useful in, for example, paper industry, textile industry, producing coatings and adhesives, painting, metal processing, resin industry, wood industry, construction industry, agriculture, forestry, fisheries, food industry and petroleum industry as well as medicine. As will be described hereinafter, the compound of the present invention exhibits an intense microbicidal effect and thus available in these fields. For example, it may be added, in an appropriate amount, to a processing water, a circulating water, a raw material or a product. Further, it may be employed for disinfecting or sterilizing facilities, plants, livestock barns or instruments as well as seeds, seedlings and raw materials.

BACKGROUND OF THE INVENTION

It is known that serious damages are caused by microorganisms in various fields. Thus, there has been urgently required to develop an effective and advantageous microbicide. For example, it is required in the field of agriculture to develop, for example, fungicides for controlling plant diseases caused by bacteria and molds, seed disinfectants and soil disinfectants. Further, there are serious problems in the field of technology. Namely, raw materials and products are contaminated or degraded with bacteria and molds, which lowers the commercial values of the products. Furthermore, the production process, facilities and environment are also contaminated therewith. It is urgently required to solve these problems.

Although some derivatives of isothiazolone are known [cf. JP-B-46 21240 (the term "JP-B" used herein means Japanese examined patent publication) corresponding to U.S Pat. No. 3,523,121 and J. Heterocyclic Chem., 8, 587 (1971)], the compound of the present invention has never been reported hitherto. In addition, every known compound is highly toxic to homeothermic animals and fishes, which significantly restricts the applications of the same.

SUMMARY OF THE INVENTION

In order to overcome the above problems, the present inventors have synthesized a number of compounds and examined the properties thereof. As a result, we have found that the novel compound represented by formula (I):

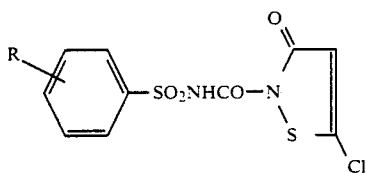

wherein R represents a lower alkyl group having 1 to 4 carbon atoms, exerts an intense microbicidal effect over a wide range of microorganisms and an excellent disinfecting and sterilizing effect and that it is hardly toxic to homeothermic animals and fishes, thus completeing the present invention.

DETAILED DESCRIPTION OF THE INVENTION

In formula (I), a lower alkyl group represented by R is preferably a methyl group.

The compound of the present invention may be readily synthesized according to a method described in, e.g., JP B-46-21240 as mentioned above. For example, it may be obtained by dissolving 5-chloro-3-hydroxyisothiazole in an appropriate solvent such as benzene or toluene, adding dropwise the equivalent amount of a 2-, 3- or 4-alkylbenzenesulfonyl isocyanate dissolved in the above solvent thereto under stirring, allowing the obtained mixture to react at room temperature and collecting the precipitate thus formed by filtration.

The compound according to the present invention exhibits an intense microbicidal activity over a wide range of microorganisms and thus is available as, for example, an agricultural fungicide for protecting seeds, seedlings, crops, harvests and agricultural materials from microbial damages. It is also available in the disinfection of, for example, agricultural facilities or culturing environment. It is further available in preventing, for example, medical facilities, residences, livestock barns, various plants or commercial facilities from microbial contamination. It is furthermore available in maintaining the qualities of industrial products such as wood, wood products, pulp, paper crafts, leather, textile, synthetic resins, coatings or adhesives or exterminating undesirable microorganisms in the process for producing the same.

When the compound of the present invention is to be employed as a microbicide, it may be used, needless to say, as such. However, it is usually blended with appropriate auxiliaries and formulated into a common microbicide form such as oil solution, emulsion, dust, wettable powder, granules or suspension. Examples of the carriers to be used include solid ones such as clay, talc, diatomaceous earth, china clay, calcium carbonate, silicic anhydride and bentonite; and liquid ones such as aromatic hydrocarbons such as xylene, aliphatic hydrocarbons such as kerosine, ketones such as methyl ethyl ketone and cyclohexanone, ethers such as anisole, alcohols such as ethanol, propanol and ethylene glycol, esters such as ethyl acetate and butyl acetate, dimethylsulfoxide, dimethylformamide and water. It is preferable to further add appropriate auxiliaries such as emulsifiers, dispersants, wetting agents or binders thereto, depending on the purpose, to thereby further ensure the effect of the composition. Examples of these auxiliaries include ionic or nonionic surfactants, carboxymethylcellulose, polyvinyl acetate, gums, stearates and waxes. Alternately, the compound of the present invention may be directly dissolved in a medium such as an adhesive or a coating or dispersed, in the form of a fine powder, therein.

The microbicide of the present invention may be employed together with other microbicides, insecticides, acaricides, herbicides and plant growth regulators such as dithiocarbamate compounds, organic iodine compounds, carbamate compounds, organic chlorine compounds, sulfamide compounds, sulfonyl urea compounds, urea compounds, thiolcabamate compounds, organic phosphate compounds, azole compounds, pyrimidine compounds, benzamide compounds, dicarbamide compounds, phthalamide compounds, antibiotics, benzimidazole compounds, benzthiazole compounds, benzisothiazole compounds, triazine compounds and quinoline compounds or applied as a mixture therewith.

The amount of the compound of the present invention used in the microbicide of the present invention may be varied over a wide range depending on the purpose. The amount generally ranges from 0.01 to 95%, preferably from 0.1 to 80% based on the total weight of the composition.

At the application of the microbicide of the present invention, the compound of the present invention or a composition thereof as described above may be applied, either as such or appropriately diluted with a medium such as water, a powder, a coating or an adhesive, other oily or aqueous or emulsion vehicle or a gas, to, for example, the surface or inside of crops or other plants, seeds, harvests, agricultural or industrial materials, production systems, industrial products, various apparatus or facilities or in the atmosphere, to the surface of inside of water, or to the surface or inside of soil in a conventional manner such as immersing, applying, coating, smearing, spraying, fuming on injecting. When the microbicide of the present invention is to be used as an agricultural fungicide, for example, in a liquid vehicle, it is effective to apply the same at ratio of 5 to 1,000 g of the active ingredient per 10 a. When it is to be used as an industrial fungicide, it is appropriate to adjust the final concentration of the active ingredient from 0.001 to 5% by weight in the vehicle.

The present invention will be illustrated in detail referring to the following examples. Thus variations and modifications may be made without departing from the spirit and scope of the present invention. In the examples, all parts refers to parts by weight, unless otherwise specified.

EXAMPLE 1

Preparation of 5-chloro-2-(N-4-tolunenesulfonylcarbamoyl)3-isothiazolone (Compound 1)

4.3 parts (0.032 mol) of 5-chloro-3-hydroxyisothiazole was dissolved in 50 parts of dry toluene and stirred at 25° C. To the resulting solution, 6.3 parts (0.032 mol) of p-toluenesulfonyl isocyanate dissolved in 20 parts of toluene was added. The pale yellow precipitate thus formed increased by continuously stirring. The pre-cipitate was collected by filtration. Thus, 9.14 parts (yield: 85.9%) of 5-chloro-2-(N-4-toluenesulfonylcarbamoyl)-3-isothiazolone (Compound 1) was obtained in the form of a pale yellow solid. m.p.: 125°–128° C.

EXAMPLE 2

Preparation of 5-chloro-2 (N-2-toluenesulfonylcarbamoyl)3-isothiazolone (Compound 2)

4.3 parts (0.032 mol) of 5-chloro-3-hydroxyisothiazole was dissolved in 50 parts of dry toluene and stirred at 25° C. To the resulting solution, 6.3 parts (0.032 mol) of o-toluenesulfonyl isocyanate dissolved in 20 parts of toluene was added. Then, the procedure of Example 1 was repeated. Thus, 8.62 parts (yield: 81.2%) of 5-chloro-2-(N-2-toluenesulfonylcarbamoyl)-3-isothiazolone (Compound 2) was obtained in the form of a brown solid. m.p.: 82° to 84° C.

EXAMPLE 3

Preparation of dust

The following components were uniformly ground and mixed to give a dust containing 3 wt% of the active ingredient.

| Component | Amount (parts by weight) |
| --- | --- |
| Compound 1 | 3.0 |
| Calcium stearate | 2.0 |
| Silicic anhydride fine powder | 0.5 |
| Clay | 94.5 |

EXAMPLE 4

Preparation of wettable powder

The following components were uniformly ground and mixed to give a wettable powder containing 30 wt% of the active ingredient.

| Component | Amount (parts by weight) |
| --- | --- |
| Compound 2 | 30 |
| Polyoxyethylene alkylaryl ether | 10 |
| Polyoxyethylene alkylaryl sulfonate | 5 |
| Silicic anhydride fine powder | 10 |
| Clay | 25 |
| Diatomaceous earth | 20 |

EXAMPLE 5

Preparation of oil solution

The following components were uniformly mixed and dissolved to give an oil solution containing 20 wt% of the active ingredient.

| Component | Amount (parts by weight) |
| --- | --- |
| Compound 1 | 20 |
| Lauryltrimethyldi(polyhydroxyethyl)ammonium chloride | 10 |
| Polyoxyethylene alkylaryl ether | 5 |
| N,N-dimethylformamide | 65 |

EXAMPLE 6

The following components were uniformly ground and mixed and an appropriate amount of water was added thereto. The resulting mixture was granulated and dried to give granules containing 10 wt% of the active ingredient.

| Component | Amount (parts by weight) |
| --- | --- |
| Compound 2 | 10 |
| Sodium lignin sulfonate | 2 |
| Carboxymethylcellulos | 1 |
| Clay | 87 |

To illustrate the effects of the invention, the following Test Examples will be given.

TEST EXAMPLE 1

2-fold serial dilutions of a solution of Compounds 1 and 2 were made with a potato agar medium on a plate. This plate was inoculated with each test microorganism which was then cultured therein at 25° C. for ten days. Then, the growth of the microorganism was examined to determine the minimum inhibitory concentration of the test compounds.

The results are shown in Table 1.

TABLE 1

| Test Microorganism | Minimum inhibitory concentration (mcg/ml) | |
|---|---|---|
| | Compound 1 | Compound 2 |
| Aspergillus niger ATCC 6275 | 25 | 25 |
| Aspergillus flavus ATCC 9643 | 12.5 | 12.5 |
| Aspergillus terreus PQMD 82J | 6.25 | 3.13 |
| Aspergillus fumigatus IAM. 3006 | 12.5 | 12.5 |
| Penicillium citrinum ATCC 9848 | 25 | 12.5 |
| Penicillium funiculosum ATCC 9644 | 12.5 | 12.5 |
| Rhizopus stlonifer K 203 | 3.13 | 3.1 |
| Mucor spinescens IAM. Mu 3 | 12.5 | 6.25 |
| Cladosporium herbarum IAM. F 517 | 3.13 | 12.5 |
| Gliocladium virens USDA T-1 | 0.78 | 0.78 |
| Chaetomium globosum ATCC 8059 | 50 | 50 |
| Pullularia pullulan IAM. F 24 | 6.25 | 6.25 |
| Tyromyces palustris | 12.5 | 6.25 |
| Coriolus versicolor | 100 | 100 |
| Xanthomonas campestris pv. oryzae | 0.2 | 0.05> |
| Pseudomonas syringae pv. tabaci | 1.56 | 0.78 |
| Pseudomonas syringae pv. lacrymans | 12.5 | 25 |
| Erwinia carotovora subsp. carotovora | 3.13 | 3.13 |
| Corynebacterium michiganense pv. michiganense | 12.5 | 12.5 |
| Pyricularia oryzae | 3.13 | 3.13 |
| Diaporthe citri | 1.56 | 3.13 |
| Colletotrichum lagenalium | 0.78 | 0.78 |
| Alternaria kikuchiana | 3.13 | 3.13 |
| Glomerella cingulata | 1.56 | 1.56 |
| Botrytis cinerea | 6.25 | 6.25 |
| Fusarium oxysporum f. lycopersici | 3.13 | 3.13 |
| Gibberella fujikuroi | 1.56 | 1.56 |
| Cochliobolus miyabeanus | 3.13 | 3.13 |
| Rhizoctonia solani sasakii type | 50 | 25 |
| Rhizoctonia solani filamentosa type | 100 | 100< |

TEST EXAMPLE 2

Disinfection against bakanae disease

Approximately 1.5 g of rice seeds (cultural variety: Nihonbare and Kinki No. 33) infected with bakanae disease (causal fungus: Gibberella fujikuroi) were weighed and introduced into a test tube. 5 ml of a solution of Compounds 1 and 2 of a definite concentration as shown in Table 2 below was poured into the test tube and thoroughly shaken. Then, the seeds were incubated at 25° C. for 24 hours. The solution of the test compound was decanted and the seeds were sowed in a raising box (30×60×5 cm). The outbreak of the disease was induced by maintaining the raising box in a phytotron at 18° to 35° C. After four weeks, namely, at the fourth to fifth leaf stage, seedlings showing elongation of third sheaths and thinned leaf blades, which were referred to suffer from bakanae disease, were counted. The inhibitory value was calculated in accordance with the following equation (II).

$$\text{Inhibitory value } (\%) = 1 - \left( \frac{\text{outbreak ratio of treated}}{\text{outbreak ratio of untreated}} \right) \times 100 \quad (II)$$

Phytotoxicity was determined by observing growth inhibition of the seedlings and necrosis of the leaves. The simbol "-" shown in Table 2 means that any phytotoxicity was not observed. A commercially available Benlate wettable powder (manufactured by du Pont, U.S.A.; containing 20% of thiuram and 20% of benomyl) was used as a control.

The results are shown in Table 2.

TABLE 2

| Cultural Variety | Compound No. | Concentration of the compound (ppm) | Numbers of infected seedlings | Numbers of total seedlings | Outbreak ratio (%) | Inhibitory value (%) | Phytotoxicity |
|---|---|---|---|---|---|---|---|
| Nipponbare | 1 | 1,000 | 1 | 53 | 1.9 | 97 | — |
| " | 1 | 500 | 2 | 66 | 3.0 | 95 | — |
| " | 1 | 250 | 17 | 70 | 24.3 | 58 | — |
| " | 2 | 1,000 | 1 | 68 | 1.5 | 97 | — |
| " | 2 | 500 | 2 | 72 | 2.8 | 95 | — |
| " | 2 | 250 | 10 | 74 | 13.5 | 86 | — |
| " | control | 1,000 | 28 | 71 | 39.4 | 31 | — |
| " | none | — | 43 | 75 | 57.3 | 0 | — |
| Kinki No. 33 | 1 | 1,000 | 1 | 67 | 1.5 | 98 | — |
| " | 1 | 500 | 3 | 70 | 4.3 | 96 | — |
| " | 1 | 250 | 5 | 73 | 6.8 | 89 | — |
| " | 2 | 1,000 | 0 | 72 | 0.0 | 100 | — |
| " | 2 | 500 | 2 | 68 | 2.9 | 95 | — |
| " | 2 | 250 | 7 | 76 | 9.2 | 85 | — |
| " | control | 1,000 | 27 | 72 | 37.5 | 37 | — |
| " | none | — | 46 | 77 | 59.7 | 0 | — |

The results shown in Table 2 obviously indicates that the compounds of the present invention are highly effective in disinfecting rice seeds.

TEST EXAMPLE 3

Disinfection against bakanae disease

The wettable powder prepared in Example 4 was diluted for a test liquid with water to each concentrations shown in Table 3. The rice seeds (cult. var.: Kinki No.33) infected with bakanae diseases (causal fungus: Gibberella fujikuroi) were subjected to the soaking treatment or the dressing treatment with the test liquid. On the soaking treatment, approximately 10 g of the rice seeds were soaked in 30 ml of the test liquid at 25° C. for 24 hours. Then, the seeds were air dryed and incubated in water to stimulate germination for 2 days. On the dressing treatment, approximately 10 g of the rice seeds were dressed uniformly with 50 mg of the wettable powder. The treated seeds were sowed in a plastic box (11 ×16×6 cm), and maintained in a phytotron. Twenty seven days after sowing, the outbreak ratio was determined and inhibitory value was computed by the equation (II). Phytotoxicity was determined in the same manner as in Test example 2. Benlate wettable powder was used as a control.

The results are shown in Table 3.

25° C. for 2 days. Sporulation of the fungi on the surface of the infected seeds was observed under microscope. The number of the infected seeds was determined and inhibitory value was computed by the equation (II).

The results are shown in Table 5.

TABLE 5

| Compound No. | Concentration of the compound (ppm) | Numbers of infected seeds | Numbers of total seeds | Outbreak ratio (%) | Inhibitory value (%) | Phyto-toxicity |
| --- | --- | --- | --- | --- | --- | --- |
| 1 | 250 | 0 | 120 | 0 | 100 | — |
| 2 | 250 | 0 | 120 | 0 | 100 | — |
| control | 1,000 | 0 | 120 | 0 | 100 | — |
| none | — | 49 | 120 | 40.8 | 0 | — |

As described above, the compound according to the present invention exerts an intense microbicidal effect over a wide range of microorganisms and is less toxic to animals than known compounds are. Thus, it can be safely employed for the improvement of undesirable symptoms and conditions caused by microorganisms in the fields of, for example, medicine, animal breeding, agriculture, forestry, fisheries, industry and environmental sanitation.

TABLE 3

| Compound No. | Treatment | Concentration of the compound | Numbers of infected seedlings | Numbers of total seedlings | Outbreak ratio (%) | Inhibitory value (%) | Phyto-toxicity |
| --- | --- | --- | --- | --- | --- | --- | --- |
| 1 | soaking | 1,000 ppm | 24 | 305 | 7.9 | 81 | — |
| " | " | 500 ppm | 55 | 340 | 16.2 | 61 | — |
| " | " | 250 ppm | 122 | 321 | 38.0 | 19 | — |
| " | dressing | 0.5 % | 25 | 351 | 7.1 | 83 | — |
| 2 | soaking | 1,000 ppm | 19 | 337 | 5.6 | 87 | — |
| " | " | 500 ppm | 57 | 366 | 15.6 | 63 | — |
| " | " | 250 ppm | 111 | 348 | 31.9 | 24 | — |
| " | dressing | 0.5 % | 18 | 357 | 5.0 | 88 | — |
| control | soaking | 1,000 ppm | 129 | 355 | 36.3 | 13 | — |
| " | dressing | 0.5 % | 38 | 362 | 10.5 | 75 | — |
| none | — | — | 144 | 344 | 41.9 | 0 | — |

TEST EXAMPLE 4

Disinfection against brown spot

The rice seeds (cult. var.: Nihonbare) infected with brown spot (causal fungus: Cochliobolus miyakeanus) were tested in the same manner as in Test Example 3 and the inhibitory value was computed by the equation (II).

The results are shown in Table 4.

While the invention has been described in detail and with reference to specific embodiments thereof, it will be apparent to one skilled in the art that various changes and modifications can be made therein without departing from the spirit and scope thereof.

What is claimed is:

1. A compound represented by formula (I)

TABLE 4

| Compound No. | Treatment | Concentration of the compound | Numbers of infected seedlings | Numbers of total seedlings | Outbreak ratio (%) | Inhibitory value (%) | Phyto-toxicity |
| --- | --- | --- | --- | --- | --- | --- | --- |
| 1 | soaking | 1,000 ppm | 2 | 342 | 0.5 | 98 | — |
| " | " | 500 ppm | 12 | 327 | 3.7 | 84 | — |
| " | " | 250 ppm | 33 | 322 | 10.2 | 55 | — |
| " | dressing | 0.5 % | 0 | 291 | 0.0 | 100 | — |
| 2 | soaking | 1,000 ppm | 3 | 336 | 0.9 | 96 | — |
| " | " | 500 ppm | 7 | 318 | 2.2 | 90 | — |
| " | " | 250 ppm | 26 | 338 | 7.7 | 66 | — |
| " | dressing | 0.5 % | 0 | 324 | 0.0 | 100 | — |
| control | soaking | 1,000 ppm | 53 | 267 | 19.9 | 13 | — |
| " | soaking | 0.5 % | 32 | 331 | 9.7 | 58 | — |
| none | — | — | 53 | 231 | 22.9 | 0 | — |

TEST EXAMPLE 5

Disinfection against rice blast

The rice seeds (cult. var.: Kusabue) infected with rice blast (causal fungus: pyricularia oryzae) were treated by the same manner as in Test Example 2. Then, the rice seeds were sowed in 9 cm-petri dish and incubated at

1.

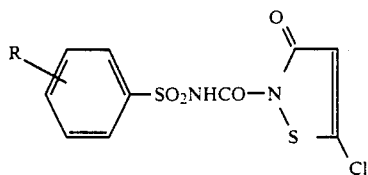

wherein R represents a lower alkyl group having 1 to 4 carbon atoms.

2. The compound according to claim 1, wherein R represents a methyl group.

3. A microbicide which comprises at least one compound represented by formula (I)

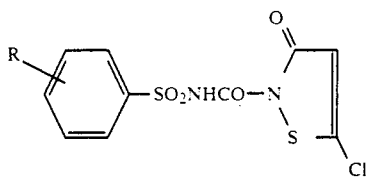

wherein R represents a lower alkyl group having 1 to 4 carbon atoms in a microbicidal effective amount and an appropriate carrier.

4. The microbicide according to claim 3, wherein the amount of the compound represented by formula (I) ranges from 0.01 to 95% based on the total weight of the microbicide.

5. A method of disinfecting seeds which comprises the step of:

applying a compound represented by formula (I) to said seeds,

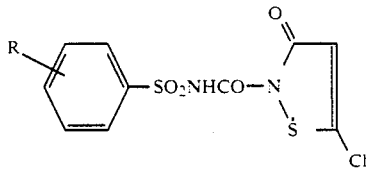

wherein R represents a lower alkyl group having 1 to 4 carbon atoms.

* * * * *